(12) United States Patent
Baudry et al.

(10) Patent No.: US 6,391,064 B1
(45) Date of Patent: May 21, 2002

(54) COMPOSITION FOR HAIR DYEING COMPRISING CONDENSATES OF QUINOLINE-5, 8-DIONES OR OF QUINOXALINE-5,8-DIONES AND SUBSTITUTED PYRROLES, ANILINES OR INDOLES

(75) Inventors: Richard Baudry, Paris; Jean Maignan, Tremblay en France; Sylvie Genard, Paris, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/386,336

(22) Filed: Aug. 31, 1999

(30) Foreign Application Priority Data

Sep. 1, 1998 (FR) ............................................ 98 10919

(51) Int. Cl.$^7$ ........................ A61K 7/13; C07D 401/00; C07D 215/12; C07D 215/16
(52) U.S. Cl. .................. 8/409; 8/423; 8/424; 546/167; 546/168; 546/173; 546/177
(58) Field of Search ............................ 8/405, 406, 407, 8/423, 424, 429, 569, 574, 409, 567; 546/167, 168, 177, 173

(56) References Cited

U.S. PATENT DOCUMENTS

| | | | |
|---|---|---|---|
| 4,602,913 A | | 7/1986 | Grollier et al. ................. 8/405 |
| 5,053,053 A | | 10/1991 | De Labbey et al. ............. 8/423 |
| 5,752,984 A | * | 5/1998 | Kneebel et al. ................. 8/423 |
| 6,022,379 A | * | 2/2000 | Genard et al. .................. 8/405 |

FOREIGN PATENT DOCUMENTS

| | | | |
|---|---|---|---|
| DE | 2441598 | * | 3/1976 |
| DE | 2441599 | * | 3/1976 |
| DE | 25 24 329 | | 12/1976 |
| DE | 2603848 | * | 8/1977 |
| DE | 2626141 | * | 12/1977 |
| DE | 2714955 | * | 10/1978 |
| EP | 0 376 776 | | 7/1990 |
| FR | 2 500 749 | | 9/1982 |

OTHER PUBLICATIONS

C. Blackburn et al., "Naphthoquinone Colouring Matters. Part 5. Reactions of NN–Dialkylarylamines with 1,4–Naphthoquinones. A Convenient Route to 2–(4–NN–Dialkylaminoaryl)–1,4–naphthoquinones", J. Chem. Research, Synopses 1982 Issue 12 (Dec.), pp. 320–321.

K. Yoshida et al., "Regioselective 6–Amination and 6–Arylation of 5,8–Quinolinedione Promoted by Metal Ions", Bull. of Chem. Soc. of Japan, vol. 61, No. 12, 1988, pp. 4335–4340.

K. Yoshida et al., "Regioselective 6–Arylation of 5,8–Quinolinedione with N–Alkyl– and N,N–Dialkyl–anilines Promoted by Metal Ions", Chem. Letters, No. 6, 1987, pp. 1191–1194.

K. Yoshida et al, "New Metallochromic and Fluorescence Compounds Obtained from the Reaction of 5,8–Quinolinedione with 2–[3–(Dimethylamino)phenyl]propene", Chem. Letters, No. 11, 1991, pp. 2027–2030.

K. Yoshida et al., "Selective Synthesis and Metallochormic Properties of Pyrrolylated Quinoline–5,8–diones", J. Chem. Soc. Perkin Trans. 1, No. 20, 1992, pp. 2713–2715.

K. Yoshida et al., "Synthesis and Properties of 6–Substituted Quinoline–5,8–diones Colour Formers", J. Chem. Soc. Perkin Trans. 1, 1994, pp. 2521–2523.

Katushira Yoshida et al., "Regioselective 6–Aminiation and 6–Arylation of 5,8–Quinolinedione Promoted by Metal Ions", Bull. Chem. Soc. Jpn., vol. 61, No. 12, 1988, pp. 4335–5340.

Chemical Abstracts, vol. 111, No. 1, Jul. 3, 1989, Abstract No. 7197.

English language Derwent Abstract of DE 25 24 329, Dec. 1976.

* cited by examiner

Primary Examiner—Margaret Einsmann
(74) Attorney, Agent, or Firm—Finnegan, Henderson, Farabow, Garrett & Dunner, L.L.P.

(57) ABSTRACT

The use of derivatives of quinoline- or quinoxaline-5,8-diones or -diols in cosmetics, especially for the dyeing of keratinous matter and, in particular, the hair. It also relates to novel compounds of this class. The invention is also directed to dyeing compositions comprising the said compounds and to the method of dyeing keratinous fibers.

17 Claims, No Drawings

COMPOSITION FOR HAIR DYEING COMPRISING CONDENSATES OF QUINOLINE-5, 8-DIONES OR OF QUINOXALINE-5,8-DIONES AND SUBSTITUTED PYRROLES, ANILINES OR INDOLES

The invention relates to the use of derivatives of quinoline- or quinoxaline-5,8-diones or -diols in cosmetics, especially for the dyeing of keratinous matter and, in particular, the hair. It also relates to novel compounds of this class. The invention is also directed to dyeing compositions comprising the said compounds and to the method of dyeing keratinous fibres.

In the literature, adducts of pyrrole compounds and N,N-dialkylarylamines or N-alkylarylamines with quinoline-5,8-diones are known.

Thus J. Griffiths and C. Blackburn, in the journal *J. Chem. Res.* (S), 1982, pages 320–321, the disclosure of which is incorporated by reference herein, studied the reactions of 1,4-naphthoquinone and its derivatives with N,N-dialkylarylamines.

In the articles by K. Yoshida et al., *Bull. Chem. Soc. Jpn.*, 1988, 61, pages 4335–4340, and *Chem. Lett.*, 1987, pages 1191–1194, the disclosures of each which are incorporated by reference herein, it was shown that, in the absence of metal salts, the reaction of quinoline-5,8-dione with N,N-dialkylarylamines was slow and led to isomer mixtures of 6- and 7-[p-(dialkylamino)phenyl]quinoline-5,8-dione whereas, in the presence of metal salts, only the compounds arylated in position 6 were obtained. The reactions are generally conducted in acetic acid; in certain cases, a chloroform-ethanol/HCl mixture can also be used, according to the article by K. Yoshida et al. in *Chem. Lett.*, 1991, 2027–2030, the disclosure of which is incorporated by reference herein.

K. Yoshida et al. in *J. Chem. Soc. Perkin Trans. I*, 1992, 2713–2715, the disclosure of which is incorporated by reference herein, also studied the dioxo-5,8-quinolylpyrroles for their physiological properties and their colouring properties on an unspecified substrate. Furthermore, in the journal *J. Chem. Soc. Perkin Trans. I*, 1994, pages 2521–2523, the disclosure of which is incorporated by reference herein, K. Yoshida et al. took an interest in quinoline-5,8-diones carrying a substituent in position 6, for the purpose of a utility as a precursor of dyes which can be used in optoelectronics.

Furthermore, the only known derivative of quinoxaline corresponds to the following formula:

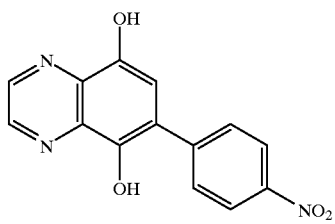

In accordance with the above text, adducts of pyrrole compounds and N,N-dialkylarylamines or N-alkylarylamines with quinoline-5,8-diones are already known, but no allusion whatsoever is made as regards their application in cosmetics.

On the other hand, the addition compounds of indoles with quinolinediones or quinoxalines are novel.

In the field of hair dyeing, dyes are sought which are reproducible, with rich and varied shades, thereby making it possible to obtain a wide pallet of colours capable of satisfying the formulator.

The inventors have now discovered that a new class of derivatives of quinoline- or quinoxaline-5,8-diones or -diols can be used for the dyeing of keratinous matter and, in particular, the hair. This new class, which is the subject of the invention, satisfies the above-described objectives and, moreover, is highly accessible, since the majority of these dyes are prepared in a single stage which is easy to implement.

The dyeings obtained with the aid of these dyes can exhibit reproducible, intensive and varied shades.

The present invention therefore provides for the use of compounds of general formulae (I) and (II) defined below in the dyeing of keratinous matter and, in particular, of the hair.

The present invention also provides novel compounds of this class.

The invention additionally provides dyeing compositions and a method of dyeing which employs them.

Other features, aspects and advantages of the invention will appear more clearly still on reading the description and various examples which follow.

One subject of the present invention is the use in the dyeing of keratinous matter and, in particular, of the hair of compounds of general formulae (I) and (II):

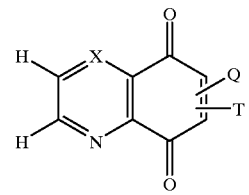
(I)

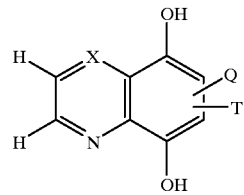
(II)

in which:

Q represents the groups

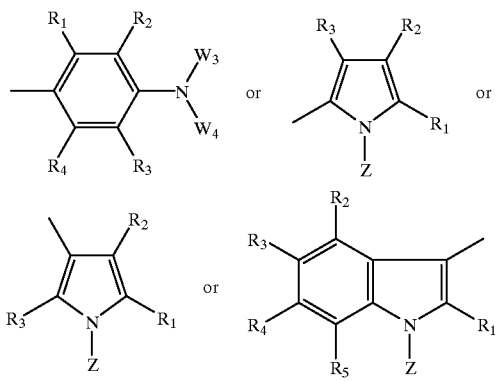

X represents the group CH or a nitrogen atom;

T represents a hydrogen atom, a halogen atom or a hydroxyl group;

$R_1$, $R_2$, $R_3$, $R_4$ and $R_5$, which are identical or different, are selected from a hydrogen atom, $C_1$–$C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, such as esters, amides, mineral salts, and organic amine salts, halogen atoms, linear and branched $C_1$–$C_4$ alkyl groups optionally substituted by a substituent selected from nitrile groups, a carboxylic acid group, derivatives of a carboxylic acid group, such as esters, amides, mineral salts, and organic amine salts, a hydroxyl group, groups such as:

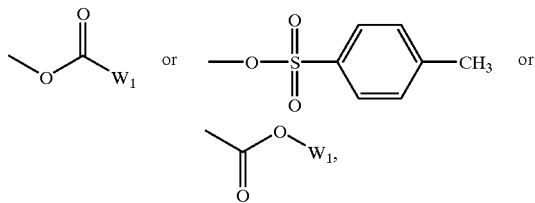

ether groups —OSi($W_1$)$_3$, amino groups

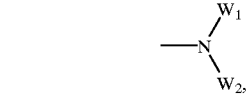

and amido groups

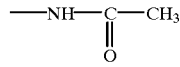

or

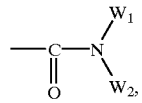

Z is selected from a hydrogen atom, a benzyl group, a phenyl group optionally substituted by a substituent selected from a hydroxyl group, groups —O—CO—$W_1$, amino groups —N($W_1$)($W_2$), groups —NH—CO—$W_1$ and a nitrile group; linear and branched $C_1$–$C_8$ alkyl groups optionally substituted by a substituent selected from a nitrile group, a carboxylic acid group, derivatives of a carboxylic acid group, such as esters, amides, mineral salts, and organic amine salts, a hydroxyl group, groups such as:

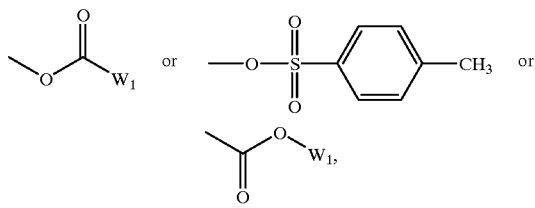

ether groups —OSi($W_1$)$_3$, amino groups

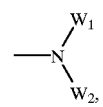

and amido groups

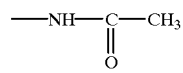

or

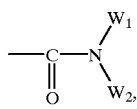

$W_1$ and $W_2$, which are identical or different, are selected from a hydrogen atom and linear and branched $C_1$–$C_4$ alkyl groups, $W_3$ and $W_4$, which are identical or different, are selected from a hydrogen atom and linear and branched $C_1$–$C_4$ alkyl groups optionally substituted by at least one substituent selected from a hydroxyl group, groups —CO—O—$W_1$, groups —O—CO—$W_1$, and amino groups —N($W_1$)($W_2$).

The $C_1$–$C_4$ alkyl groups or the $C_1$–$C_4$ alkyl moieties of alkoxy groups can be linear or branched and are selected in particular from the groups methyl, ethyl, n-propyl, isopropyl, n-butyl, isobutyl and tert-butyl, preferably from the groups methyl, ethyl and n-butyl.

The $C_1$–$C_8$ alkyl groups can be linear or branched; they can be substituted by a nitrile group, a carboxylic acid group or its derivatives such as esters, amides, mineral salts and organic amine salts, a hydroxyl group, an ester group such as alkoxycarbonyl, carboxyl, alkylcarbonyloxy, formyloxy, tosyloxy, an amino group, an amido group such as aminocarbonyl or acetamido, or an ether group selected from trialkylsiloxy and siloxy groups.

These $C_1$–$C_8$ alkyl groups are selected in particular from the groups methyl, ethyl, n-propyl, isopropyl, n-butyl, isobutyl, tert-butyl, pentyl, hexyl, heptyl and octyl, and preferably from the groups methyl and pentyl.

The halogen atoms are selected from chlorine, bromine, fluorine and iodine, and in particular chlorine.

Among the compounds of formulae (I) and (II) defined above, mention may be made in particular of the following compounds:

6-(1-pentyl-1H-pyrrol-2-yl)quinoline-5,8-dione,
6-(1-benzyl-1H-pyrrol-2-yl)quinoline-5,8-dione,
methyl 4-(5,8-dioxo-5,8-dihydroquinolin-6-yl)-2,5-dimethyl-1H-pyrrole-3-carboxylate,
N-[2-[2-(5,8-dioxo-5,8-dihydroquinolin-6-yl)pyrrol-1-yl]ethyl]acetamide,
6-(1-phenyl-1H-pyrrol-2-yl)quinoline-5,8-dione,
3-[2-(5,8-dioxo-5,8-dihydroquinolin-6-yl)pyrrol-1-yl]propionitrile,
6-chloro-7-(1-methyl-1H-pyrrol-2-yl)quinoline-5,8-dione,
6-(1,2-dimethyl-1H-indol-3-yl)quinoline-5,8-dione,
6-(1-benzyl-1H-indol-3-yl)quinoline-5,8-dione, 6-(2-phenyl-1H-indol-3-yl)quinoline-5,8-dione,
6-(2-methyl-1H-indol-3-yl)quinoline-5,8-dione,
6-(2-methyl-1H-indol-3-yl)quinoline-5,8-dione,
6-[p-(N,N-(2-diacetyloxyethyl)amino)phenyl]-quinoline-5,8-dione,
6-(1-methyl-1H-pyrrol-2-yl)quinoxaline-5,8-dione,
6-(1-methyl-1H-pyrrol-2-yl)quinoline-5,8-dione,
7-(1-methyl-1H-pyrrol-2-yl)quinoline-5,8-dione,
6-[p-(N,N-diethylamino)phenyl]quinoline-5,8-dione,
6-[p-(N,N-dimethylamino)phenyl]quinoline-5,8-dione
7-[p-(N,N-dimethylamino)phenyl]quinoline-5,8-dione
6-[4-(N,N-diethylamino)-3-isopropenylphenyl]-quinoline-5,8-dione,
6-[4-(N,N-diethylamino)-3-(N-acetylamino)phenyl]quinoline-5,8-dione,
6-[4-(N, N-dimethylamino)-3-isopropenylphenyl]-quinoline-5,8-dione,
6-[4-(N,N-di-n-butylamino)-3-hydroxyphenyl]-quinoline-5,8-dione,
6-[p-(N-n-butylamino)phenyl]quinoline-5,8-dione,
6-[p-(N-methylamino)phenyl]quinoline-5,8-dione,
6-(1-methyl-1H-pyrrol-2-yl)quinoline-5,8-diol,
7-(1-methyl-1H-pyrrol-2-yl)quinoline-5,8-diol.

Among the compounds of formulae (I) and (II) which can be used in the present invention, more particular preference is given to the derivatives of formula (I) or (II) for which X represents CH; T represents H; Q is selected from:

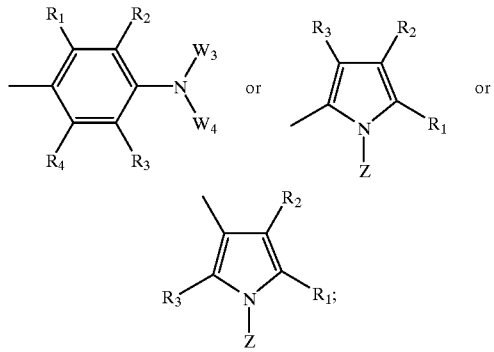

$R_1$ represents H or —OH; $R_2$, $R_3$, $R_4$ and $R_5$ each represent H; Z represents H or $CH_3$, phenyl, benzyl or 2-cyanoethyl; and $W_3$ and $W_4$ are selected from H and the groups methyl, ethyl and n-butyl.

The novel compounds correspond to the formulae (I) and (II) of the invention, with the proviso that:

when Q represents

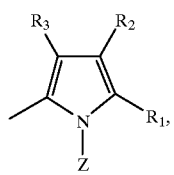

X=C and T=H, then Z is other than the methyl group;

when Q represents

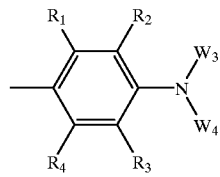

and one of the substituents $W_3$ and $W_4$ represents a hydrogen atom, the other substituent does not represent a methyl or n-butyl group; and when Q represents

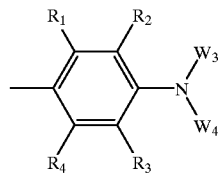

and the substituents $W_3$ and $W_4$ are identical, they do not represent either a methyl group or an ethyl group.

These compounds can be defined by the general formulae (III) and (IV):

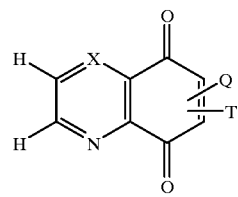

(III)

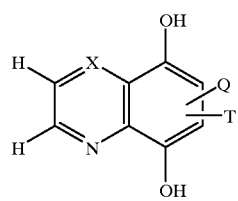

(IV)

in which Q represents

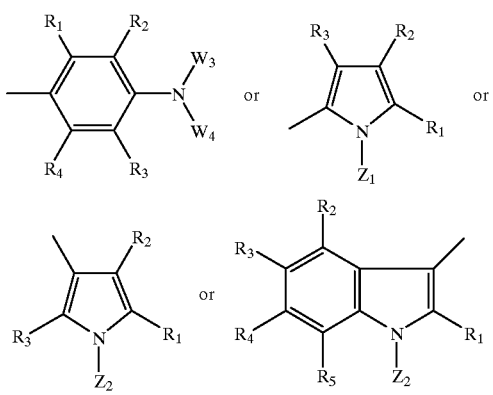

X represents the group CH or a nitrogen atom;

T represents a hydrogen atom, a halogen atom or a hydroxyl group;

$R_1$, $R_2$, $R_3$, $R_4$ and $R_5$, which are identical or different, are selected from a hydrogen atom, $C_1-C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, such as esters, amides, mineral salts, and organic amine salts, halogen atoms, linear and branched $C_1-C_4$ alkyl groups optionally substituted by a substituent selected from a nitrile group, a carboxylic acid group, derivatives of a carboxylic acid group, such as esters, amides, mineral salts and organic amine salts, a hydroxyl group, groups such as:

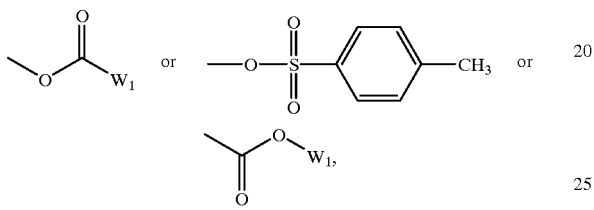

ether groups —OSi($W_1$)$_3$, amino groups

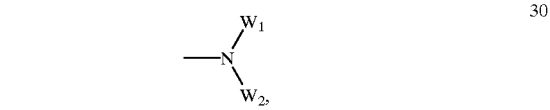

amido groups

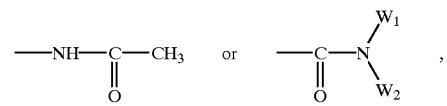

$Z_2$ represents a hydrogen atom, a benzyl group, a phenyl group optionally substituted by a substituent selected from a hydroxyl group, groups —CO—O—$W_1$, groups —O—CO—$W_1$, amino groups —N($W_1$)($W_2$), amino groups —CO—N($W_1$)($W_2$), amino groups —NH—CO—$W_1$ and a nitrile group; linear and branched $C_1-C_8$ alkyl groups optionally substituted by a substituent selected from a nitrile group, a carboxylic acid group, derivatives of a carboxylic acid group, such as esters, amides, mineral salts, and organic amine salts, a hydroxyl group, groups such as:

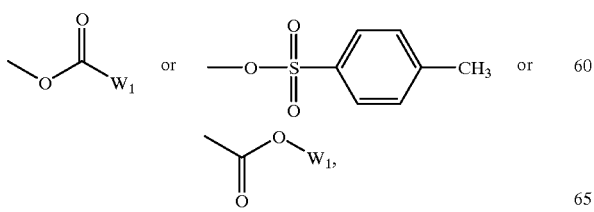

ether groups —OSi($W_1$)$_3$, amino groups

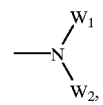

amido groups

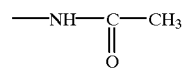

or

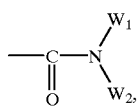

$Z_1$ has the same meanings as $Z_2$ with the proviso that $Z_1$ is not methyl in the cases where T=H and X=CH, $W_1$ and $W_2$, which are identical or different, are selected from a hydrogen atom and linear and branched $C_1-C_4$ alkyl groups, $W_4$ is selected from a hydrogen atom and linear and branched $C_1-C_4$ alkyl groups, optionally substituted by at least one substituent selected from a hydroxyl group, groups —CO—O—$W_1$, groups —O—CO—$W_1$, and amino groups —N($W_1$)($W_2$), and $W_3$ has the same meanings as $W_4$ with the proviso that, when one of the substituents $W_3$ and $W_4$ represents a hydrogen atom, the other substituent does not represent a methyl or n-butyl group; and, when the substituents $W_3$ and $W_4$ are identical, they do not represent either a methyl group or an ethyl group.

Among the novel compounds of formulae (III) and (IV) defined above, mention may be made in particular of the following compounds:

6-(1-pentyl-1H-pyrrol-2-yl)quinoline-5,8-dione,
6-(1-benzyl-1H-pyrrol-2-yl)quinoline-5,8-dione,
methyl 4-(5,8-dioxo-5,8-dihydroquinolin-6-yl)-2,5-dimethyl-1H-pyrrole-3-carboxylate,
N-[2-[2-(5,8-dioxo-5,8-dihydroquinolin-6-yl)pyrrol-1-yl]ethyl]acetamide,
6-(1-phenyl-1H-pyrrol-2-yl)quinoline-5,8-dione,
3-[2-(5,8-dioxo-5,8-dihydroquinolin-6-yl)pyrrol-1-yl]propionitrile,
6-chloro-7-(1-methyl-1H-pyrrol-2-yl)quinoline-5,8-dione,
6-(1,2-dimethyl-1H-indol-3-yl)quinoline-5,8-dione,
6-(1-benzyl-1H-indol-3-yl)quinoline-5,8-dione,
6-[p-(N,N-(2-diacetyloxyethyl)amino)phenyl]-quinoline-5,8-dione,
6-(2-phenyl-1H-indol-3-yl)quinoline-5,8-dione,
6-(1-methyl-1H-indol-3-yl)quinoline-5,8-dione,
6-(2-methyl-1H-indol-3-yl)quinoline-5,8-dione,
6-(1-methyl-1H-pyrrol-2-yl)quinoxaline-5,8-dione.

Among the compounds of formulae (III) and (IV) which can be used in the present invention, more particular preference is given to the derivatives of formula (III) or (IV) in which X represents CH or N; T represents H; Q is selected from:

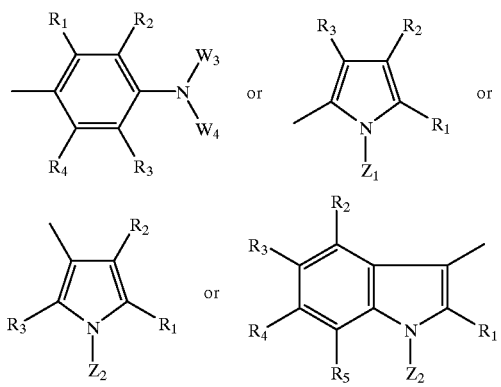

$R_1$ is selected from H and the —$CH_3$ group; $R_2$ represents H or the group —COO—$W_1$, $R_3$ represents H or the methyl group, $R_4$ and $R_5$ each represent H; $W_1$ represents the —$CH_3$ group; $Z_1$ represents —$C_5H_{11}$, —$(CH_2)_2$—NH—$COCH_3$, —$(CH_2)_2$—CN or phenyl; $Z_2$ represents H or the —$CH_3$ and benzyl groups; and $W_3$ and $W_4$ can represent the group —$(CH_2)_2OCOW_1$.

The inventors have discovered that it is possible to dye keratinous fibres and, in particular, the hair by virtue of the compounds of formulae I and II. The colours obtained depend on the nature of the substituents Q and T that are used for carrying out the synthesis. By varying the nature of these substituents it is possible to produce a range of varied colours.

In accordance with the invention, the compounds of formula (I) or (II) are used for the direct dyeing, also known as semi-permanent colouring, of keratinous fibres and, in particular, the hair.

The compounds of formula (I) or (II) can be introduced as direct dyes into oxidation dyeing compositions to enrich with glints the dyeings obtained by means of the oxidation dye precursors and, optionally, of the couplers which are generally used in this type of dyeing.

The compounds of formula (II) are capable of being oxidized by atmospheric oxygen and are used for the dyeing of keratinous fibres, in particular the hair, in accordance with the method known as progressive dyeing, which comprises applying the compound of formula (II) to the fibres, in leaving it in the air generally for from 5 to approximately 45 minutes and, preferably, from 5 to approximately 30 minutes, on the said fibres, and in repeating this operation the desired number of times until, preferably, the desired coloration is obtained.

The invention also provides a dyeing composition, in particular a cosmetic dyeing composition, for keratinous matter and, in particular, for human keratinous fibres, which comprises, in a medium appropriate for dyeing, an effective amount of at least one of the compounds of formula (I) or (II) defined above.

For the purposes of the invention, the term keratinous matter refers principally to natural textile fibres such as wool and animal fur, the term human keratinous matter refers to the skin and nails, and the term human keratinous fibres refers to the hair, the eyebrows and the eyelashes. The invention is directed still more particularly to the hair of the head.

The compounds of formula (I) or (II) are generally present in proportions of between approximately 0.01 and 10%, inclusive, preferably between approximately 0.05 and 5%, inclusive, by weight, relative to the total weight of the dyeing composition.

The cosmetically acceptable medium is preferably a medium comprising water and/or organic solvents which are acceptable from the standpoint of cosmetology if the composition is intended for use in cosmetics, and, more particularly, alcohols (ethyl alcohol, isopropyl alcohol, benzyl alcohol), glycols or glycol ethers (propylene glycol or its ethers such as, for example, propylene glycol monomethyl ether, butylene glycol, dipropylene glycol and diethylene glycol alkyl ethers, such as, for example, diethylene glycol monoethyl ether or monobutyl ether, and ethylene glycol monomethyl, monoethyl and monobutyl ethers) in concentrations of generally between 0.5 and 25%, inclusive, preferably, between approximately 2 and 15%, inclusive, by weight relative to the total weight of the composition. The cosmetically acceptable medium may also include fats such as oils and waxes.

Fatty amides, such as mono- and diethanolamides and acids derived from copra, lauric acid or oleic acid, may also be added to the composition according to the invention, in concentrations of between approximately 0.05 and 10%, inclusive, by weight.

In order to obtain varied shades, the dyeing composition according to the invention may also include, in addition to the dyes of formula (I) or (II), one or more other direct dyes which are conventionally used, and in particular nitro-functional benzenic dyes, such as nitrophenylenediamines, nitrodiphenylamines, nitroanilines, nitro-functional phenol ethers or nitrophenols, nitropyridines, anthraquinone dyes, monoazo or disazo dyes, triarylmethane dyes, azine dyes, acridine dyes and xanthene dyes, or else metallic dyes. The proportion of all these other direct dyes of addition can vary between 0.05 and 10%, inclusive, by weight relative to the total weight of the dyeing composition.

The said dyeing composition may additionally comprise any other adjuvant which is used commonly in the dyeing of keratinous matter, and, for example, surfactants which are well known in the prior art and are of anionic, cationic, nonionic, amphoteric or zwitterionic type, or mixtures thereof, thickeners, antioxidants, perfumes, sequestrants, dispersants, conditioning agents, preservatives, opacifiers, etc.

The person skilled in the art will of course take care to select the above-mentioned complementary compound or compounds such that the advantageous properties intrinsic to the dyeing composition according to the invention are not, or not substantially, adversely affected by the intended addition or additions.

The dyeing composition according to the invention can be formulated at an acidic, neutral or alkaline pH, it being possible for the pH to vary, for example, from 2 to 11 and, preferably, from 2.5 to 10, and to be adjusted by means of basifying or acidifying agents which are well known in the prior art.

Among the basifying agents, mention may be made, by way of example, of aqueous ammonia, alkali metal carbonates, alkanolamines such as mono-, di- and triethanolamines and their derivatives, sodium hydroxide or potassium hydroxide, and the compounds of the following formula:

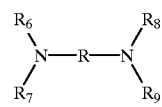

in which R represents a propylene group which is optionally substituted by a hydroxyl group or a $C_1$–$C_4$ alkyl group; and $R_6$, $R_7$, $R_8$ and $R_9$, which are identical or different, are selected from a hydrogen atom, $C_1$–$C_4$ alkyl groups and $C_1$–$C_4$ hydroxyalkyl groups.

The acidifying agents which are used are conventionally known. Mention may be made, by way of example, of mineral acids or organic acids, such as hydrochloric acid, ortho-phosphoric acid, carboxylic acids such as tartaric acid, citric acid or lactic acid, and sulphonic acids.

When the composition is intended to be applied to human keratinous fibres, it can be presented in various forms, such as in the form of a liquid, cream or gel or any other form appropriate for carrying out the dyeing of keratinous fibres. In particular, it can be packaged under pressure in an aerosol can in the presence of a propellant, and can form a foam.

Another subject of the present invention relates to a method of dyeing human keratinous fibres and, more particularly, the hair by direct dyeing, which comprises leaving a dyeing composition comprising at least one compound of formula (I) or (II) to act on wet or dry keratinous fibres. The composition according to the invention can be used as a non-rinse composition; in other words, following application of the composition to the fibres, drying is carried out without rinsing beforehand. In the other modes of application, the composition is left to act on the fibres for a period generally varying between 3 and 60 minutes, inclusive, approximately, preferably between 5 and 45 minutes, inclusive, and the fibres are rinsed, optionally washed and rinsed again, and then dried.

An additional subject of the present invention relates to a method of progressive dyeing which comprises applying a dyeing composition comprising a compound of formula (II) defined above to the keratinous fibres, leaving the said composition in air for generally 5 to approximately 45 minutes and, preferably, from 5 to approximately 30 minutes, and then rinsing the fibres, optionally washing them, then rinsing them again, and then drying them.

By way of illustration and without any limitative character whatsoever, a number of examples will now be given of the preparation of compounds of formula (I) or (II) according to the invention, along with specific examples of dyeing compositions based on such compounds.

In order to prepare the compounds of formulae (I) to (IV), use is made generally of the procedure described by K. Yoshida, Y. Ueno, M. Suzuki, Y. Yoshida and Y. Kubo in *J. Chem. Soc. Perkin Trans. I*, 1992, 2713–2715, the disclosure of which is incorporated by reference herein, by reaction of quinoline-5,8-dione with a pyrrole derivative, selecting an appropriate molar ratio between the two reactants in solvent medium.

PREPARATION EXAMPLES

The compounds of the following examples were prepared with the aid of the general procedure described by K. Yoshida, Y. Ueno, M. Suzuki, Y. Yoshida and Y. Kubo in J. Chem. Soc. Perkin Trans. I, 1992, 2713–2715. This procedure was used for Examples 1 to 7.

A pyrrole derivative (25.12 mmol) and quinoline-5,8-dione in 50 ml of chloroform are added at room temperature to a solution of 3.14 mmol of ferric chloride in 60 ml of 20% aqueous acetic acid solution. The reaction medium is maintained with vigorous stirring and the progress of the reaction is monitored by thin-layer chromatography. At the end of the reaction, the organic phase is separated off, and the aqueous phase is extracted with 2×30 ml of chloroform. The combined organic phases are washed with aqueous sodium carbonate solution and then with water before being dried over magnesium sulphate, filtered and concentrated under reduced pressure. The crude product thus obtained is purified by chromatography on a silica gel column.

Example 1

Preparation of 6-(1-Methyl-1H-pyrrol-2-yl) quinoline-5,8-dione

The compound of Example 1 is prepared following the procedure described above. After 5 minutes of reaction, 6-(1-methyl-1H-pyrrol-2-yl)quinoline-5,8-dione is isolated. The yield is 62%.

The structure of the compound was verified by $^1$H and $^{13}$C NMR spectroscopy.

$^1$H NMR, 200 MHz (CDCl$_3$, δ ppm): 3.73 (s, 3H), 6.30 (d.d, 1H), 6.77 (d.d, 1H), 6.94 (m, 1H), 7.03 (s, 1H), 7.70 (d.d, 1H), 8.49 (d, 1H), 9.05 (d, 1H). $^{13}$C NMR, 50 MHz (CDCl$_3$, δ ppm): 36.4; 109.9; 118.5; 125.9; 127.4; 129.5; 130.2; 131.0; 135.1; 136.4; 138.6; 154.6; 183.0; 183.9. Melting point: 167–168° C.

Example 2

Preparation of 6-(1-Pentyl-1H-pyrrol-2-yl) quinoline-5,8-dione

After 5 minutes of reaction, 6-(1-pentyl-1H-pyrrol-2-yl) quinoline-5,8-dione is isolated, in accordance with the above procedure, in the form of an oil. The yield is 18%.

$^1$H NMR, 200 MHz (CDCl$_3$, δ ppm): 0.83 (t, 3H), 1.22 (m, 4H), 1.73 (q, 2H), 3.96 (t, 2H), 6.30 (d.d, 1H), 6.67 (d.d, 1H), 7.00 (m, 2H), 7.70 (d.d, 1H), 8.49 (d.d, 1H), 9.05 (d.d, 1H).

Example 3

Preparation of 6-(1-Benzyl-1H-pyrrol-2-yl) quinoline-5,8-dione

After 5 minutes of reaction, 6-(1-benzyl-1H-pyrrol-2-yl) quinoline-5,8-dione is isolated in accordance with the above procedure. The yield is 53%.

$^1$H NMR, 200 MHz (CDCl$_3$, δ ppm): 5.21 (s, 2H), 6.36 (d.d, 1H), 6.73 (d.d, 1H), 6.92 (s, 1H), 6.93–7.01 (m, 3H), 7.18–7.24 (m, 3H), 7.68 (d.d, 1H), 8.47 (d.d, 1H), $^{13}$C NMR, 50 MHz (CDCl$_3$, δ ppm): 52.3; 110.0; 118.0; 126.0; 126.7; 127.4; 127.9; 128.8; 129.3; 131.9; 135.0; 137.1; 139.4; 147.4; 154.5; 183.0; 183.9. Melting point: 172–173° C.

Example 4

Preparation of Methyl 4-(5,8-Dioxo-5,8-dihydroquinolin-6-yl)-2,5-dimethyl-1H-pyrrole-3-carboxylate After 5 hours of reaction, methyl 4-(5,8-dioxo-5,8-dihydroquinolin-6-yl)-2,5-dimethyl-1H-pyrrole-3-carboxylate is isolated in accordance with the above procedure. The yield is 58%.

$^1$H NMR, 200 MHz (CDCl$_3$, δ ppm): 2.25 (s, 3H), 2.52 (s, 3H), 3.63 (s, 3H), 6.94 (s, 1H), 7.70 (d.d, 1H), 8.36 (m, 1H), 8.48 (d.d, 1H), 9.05 (d.d, 1H). Melting point: 237–241° C.

Example 5

Preparation of N-[2-[2-(5,8-Dioxo-5,8-dihydroquinolin-6-yl)pyrrol-1-yl]ethyl]acetamide After 20 minutes of reaction, N-[2-[2-(5,8-dioxo-5,8-dihydroquinolin-6-yl)pyrrol-1-yl]ethyl]-acetamide is isolated in accordance with the above procedure. The yield is 41%.

¹H NMR, 200 MHz (CDCl₃, δ ppm): 1.89 (s, 3H), 3.51 (m, 2H), 4.13 (t, 2H), 5.90 (s large, 1H), 6.33 (d.d, 1H), 6.61 (d.d, 1H), 7.00–7.03 (m, 2H), 7.71 (d.d, 1H), 8.48 (d.d, 1H), 9.04 (d.d, 1H). Melting point: 164–165° C.

Example 6

Preparation of 6-(1-Phenyl-1H-pyrrol-2-yl) quinoline-5,8-dione

After 6 hours of reaction, 6-(1-phenyl-1H-pyrrol-2-yl) quinoline-5,8-dione is isolated in accordance with the above procedure. The yield is 64%.

¹H NMR, 200 MHz (CDCl₃, δ ppm): 6.44–6.48 (m, 2H), 6.93 (d.d, 1H), 7.31–7.47 (m, 6H), 7.81 (d.d, 1H), 8.27 (d.d, 1H), 8.99 (d.d, 1H). ¹³C NMR, 50 MHz (CDCl₃, δ ppm): 111.1; 120.4; 125.0; 125.1; 127.4; 127.8; 129.5; 129.8; 130.2; 131.7; 135.0; 138.3; 139.9; 147.4; 154.5; 182.7; 183.8. Melting point: 132–134° C.

Example 7

Preparation of 3-[2-(5,8-Dioxo-5,8-dihydroquinolin-6-yl)pyrrol-1-yl]propionitrile.

After 30 minutes of reaction, 3-[2-(5,8-dioxo-5,8-dihydroquinolin-6-yl)pyrrol-1-yl]propionitrile is isolated in accordance with the above procedure. The yield is 44%.

¹H NMR, 200 MHz (CDCl₃, δ ppm): 2.88 (t, 2H), 4.22 (t, 2H), 6.37 (d.d, 1H), 6.59 (d.d, 1H), 7.08–7.11 (m, 2H), 7.73 (d.d, 1H), 8.50 (d.d, 1H), 9.08 (d.d, 1H). ¹³C NMR, 50 MHz (CDCl₃, δ ppm): 20.2; 44.0; 111.2; 117.0; 117.4; 126.1; 127.6; 127.7; 129.2; 134.2; 135.2; 139.4; 147.5; 154.9; 182.9; 184.1. Melting point: 166–167° C.

Example 8

Preparation of 6-(1-Methyl-1H-pyrrol-2-yl) quinoline-5,8-diol 6-(1-Methyl-1H-pyrrol-2-yl)quinoline-5,8-diol was prepared in accordance with the procedure described by K. Yoshida et al. in the article in *J. Chem. Perkin Trans. I*, 1994, 2521–2523.

Melting point: 142–143° C.

Example 9

Preparation of 6-Chloro-7-(1-methyl-1H-pyrrol-2-yl)quinoline-5,8-dione

A solution of 2.58 mmol of 6-chloroquinoline-5,8-dione with 20.7 mmol of 1-methylpyrrole in 50 ml of acetic acid is stirred at room temperature for 24 hours. The medium is subsequently concentrated under reduced pressure, the residue is extracted with chloroform and the combined organic phases are washed in succession with aqueous sodium carbonate solution and then water before being dried over magnesium sulphate, filtered and concentrated under vacuum. The crude product obtained is purified by chromatography on a silica gel column to give 6-chloro-7-(1-methyl-1H-pyrrol-2-yl)quinoline-5,8-dione with a yield of 40%.

¹H NMR, 200 MHz (CDCl₃, δ ppm): 3.57 (s, 3H), 6.34 (d.d, 1H), 6.61 (d.d, 1H), 6.94 (t, 1H), 7.75 (d.d, 1H), 8.56 (d.d, 1H), 9.10 (d.d, 1H). Melting point: 168–169° C.

Examples 10 to 14 describe the condensation of indoles onto the quinoline-5,8-dione ring system. The monocondensation was verified by mass spectrometry.

Example 10

Preparation of 6-(1,2-Dimethyl-1H-indol-3-yl) quinoline-5,8-dione

The product is prepared in accordance with the general procedure of Examples 1 to 7 with a yield of 46%.

Melting point: 213–214° C.

Example 11

Preparation of 6-(1-Benzyl-1H-indol-3-yl)quinoline-5,8-dione

The product is prepared in accordance with the general procedure with a yield of 51%.

Melting point: 179–180° C.

Example 12

Preparation of 6-(2-Phenyl-1H-indol-3-yl)quinoline-5,8-dione

The product is prepared in accordance with the general procedure with a yield of 62%.

Melting point: 330° C. (decomposition).

Example 13

Preparation of 6-(1-Methyl-1H-indol-3-yl)quinoline-5,8-dione

The product is prepared in accordance with the general procedure with a yield of 54%.

Melting point: 215–217° C.

Example 14

Preparation of 6-(2-Methyl-1H-indol-3-yl)quinoline-5,8-dione

The product is prepared in accordance with the general procedure with a yield of 58%.

Melting point: 221–223° C.

The procedure used for the preparation of the 6-[p-(dialkylamino)phenyl]quinoline-5,8-diones of Examples 15 and 16 is that described by K. Yoshida et al. in the article in *Bull. Chem. Soc. Jap.* 1988, 61, 4335.

Example 15

Preparation of 6-[p-(Diethylamino)phenyl] quinoline-5,8-dione

The product is prepared in accordance with the above procedure with a yield of 78%.

¹H NMR, 200 MHz (DMSO d₆, δ ppm): 1.20 (t, 6H), 3.44 (q, 4H), 6.72 (d, 2H), 7.18 (s, 1H), 7.62 (d, 2H), 7.62 (d.d, 1H), 8.50 (d.d, 1H), 9.04 (d.d, 1H). Melting point: 136–137° C.

Example 16

Preparation of 6-[p-(N,N-(2-diacetyloxyethyl) amino)phenyl]quinoline-5,8-dione

The product is prepared in accordance with the above procedure with a yield of 64%. It is isolated in the form of a viscous, dark violet oil.

¹H NMR, 200 MHz (DMSO d₆, δ ppm): 2.53 (s, 6H), 3.62–3.68 (m, 4H), 4.24–4.27 (m, 4H), 6.76–6.88 (m, 2H), 7.11–7.26 (m, 2H), 7.59–7.72 (m, 2H), 8.49–8.53 (m, 1H), 9.06 (m, 1H).

Example 17

Preparation of 6-(1-Methyl-1H-pyrrol-2-yl)quinoxaline-5,8-dione 0.81 g of N-methylpyrrole and 200 mg of quinoxaline-5,8-dione in solution in 50 ml of chloroform are added rapidly to a solution of 338 mg of $FeCl_3 \times 6H_2O$ in a water (48 ml)/acetic acid (12 ml) mixture. The medium is stirred vigorously for 10 minutes and then the organic phase is separated off.

The aqueous phase is extracted twice with chloroform, and the combined organic phases are washed with aqueous sodium carbonate solution and then water before being dried over magnesium sulphate, filtered and concentrated under vacuum. The residue thus obtained is purified by chromatography on a silica gel column to give 6-(1-methyl-1H-pyrrol-2-yl)quinoxaline-5,8-dione with a yield of 68%.

$^1$H NMR, 200 MHz ($CDCl_3$, δ ppm): 3.77 (s, 3H), 6.34 (d.d, 1H), 6.88 (d.d, 1H), 6.99 (m, 1H), 7.13 (s, 1H), 9.05 (s, 2H). Melting point: 161–162° C.

EXAMPLES OF DYEING COMPOSITIONS

Examples of Dyeing at an Acidic pH

The general formulation at acid pH is as follows:

|  | Amount |
| --- | --- |
| Compound from Preparation Example (see Table 1) | $2.24 \times 10^{-3}$ mol |
| Benzyl alcohol | 10 g |
| Ethyl alcohol | 21 g |
| Glycerol | 5 g |
| Hydroxyethylcellulose sold by the company Union Carbide under the name CELLOSIZE QP 4400 H | 2.3 g |
| Citric acid | 1.4 g |
| Water q.s. to | 100 g |

The dyeing procedure comprises applying the preparation, whose pH is approximately 3, at room temperature to natural grey hair, permed or otherwise, or to bleached hair, in a proportion of 3 grams per gram of hair. After having left the composition to act for 30 minutes, the locks were rinsed and then dried. The dyeing results are collated in Table 1.

TABLE 1

| Test compound | Mass in g % | Natural grey hair | Bleached hair | Permed grey hair |
| --- | --- | --- | --- | --- |
| Compound of Ex. 3 | 0.704 |  | rosewood |  |
| Compound of Ex. 15 | 0.686 | blue | blue | blue |
| Compound of Ex. 4 | 0.695 |  | rosewood |  |
| Compound of Ex. 5 | 0.693 |  | strawberry |  |
| Compound of Ex. 6 | 0.673 | rosewood | orange-red | rosewood |
| Compound of Ex. 7 | 0.621 |  | pale pink |  |
| Compound of Ex. 9 | 0.611 |  | pinky beige |  |
| Compound of Ex. 1 | 0.534 | rosewood | dark-purplish red | rosewood |

Examples of Dyeing at a pH of 7.5

The general formulation at pH 7.5 is as follows:

|  | Amount |
| --- | --- |
| Compound from Preparation Example (see Table 2) | $2.24 \times 10^{-3}$ mol |
| Benzyl alcohol | 10 g |
| Ethyl alcohol | 21 g |
| Glycerol | 5 g |
| Hydroxyethylcellulose sold by the company Union Carbide under the name CELLOSIZE QP 4400 H | 2.3 g |
| $K_2HPO_4/KH_2PO_4$ (1.5M/1M) buffer | 10 g |
| Water q.s. to | 100 g |

The dyeing procedure comprises applying the preparation, whose pH is approximately 7.5, at room temperature to natural grey hair, permed or otherwise, or to bleached hair, in a proportion of 3 grams per gram of hair. After having left the composition to act for 30 minutes, the locks were rinsed and then dried. The dyeing results are collated in Table 2.

TABLE 2

| Test compound | Mass in g % | Natural grey hair | Bleached hair | Permed grey hair |
| --- | --- | --- | --- | --- |
| Compound of Ex. 15 | 0.686 | green-blue | blue | blue |
| Compound of Ex. 1 | 0.534 | rosewood | dark-purplish red | rosewood |

Examples of Dyeing at Basic pH

The general formulation at pH 8.6 is as follows:

|  | Amount |
| --- | --- |
| Compound from Preparation Example (see Table 3) | $2.24 \times 10^{-3}$ mol |
| Benzyl alcohol | 10 g |
| Ethyl alcohol | 21 g |
| Glycerol | 5 g |
| Hydroxyethylcellulose sold by the company Union Carbide under the name CELLOSIZE QP 4400 H | 2.3 g |
| Aminopropanediol/HCl (1M/0.035M) buffer | 10 g |
| Water q.s. to | 100 g |

The dyeing procedure comprises applying the preparation, whose pH is approximately 8.6, at room temperature to natural grey hair, permed or otherwise, or to bleached hair, in a proportion of 3 grams per gram of hair. After having left the composition to act for 30 minutes, the locks were rinsed and then dried. The dyeing results are collated in Table 3.

TABLE 3

| Test compound | Mass in g % | Natural grey hair | Bleached hair | Permed grey hair |
| --- | --- | --- | --- | --- |
| Compound of Ex. 15 | 0.686 | green-blue | blue | blue |
| Compound of Ex. 1 | 0.534 | rosewood | dark-purplish red | rosewood |

What is claimed is:

1. A composition for the dyeing of keratin fibers comprising a cosmetically acceptable medium and an amount effective for dyeing keratin fibers of at least one dye chosen from general formulae (I) and (II) below:

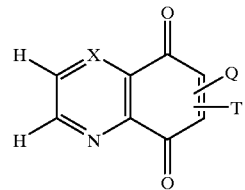
(I)

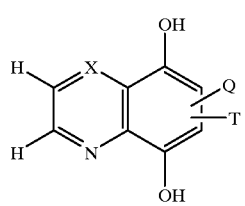
(II)

wherein:

T is chosen from a hydrogen atom, halogen atoms and a hydroxyl group;

X is chosen from a —CH group and a nitrogen atom;

Q is chosen from the groups below:

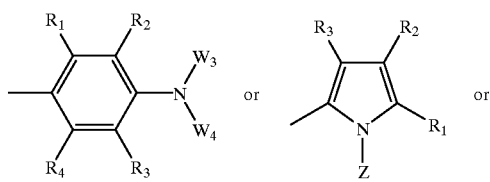

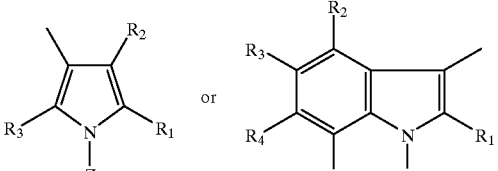

wherein in said groups:

$R_1$, $R_2$, $R_3$, $R_4$ and $R_5$, which are identical or different, are selected from a hydrogen atom, $C_1$-$C_4$ alkoxy groups, amino groups —N(W$_1$)(W$_2$), groups —NH—CO—W$_1$, groups —O—CO—W$_1$, a hydroxyl group, a carboxylic acid group, derivatives of a carboxylic acid group, halogen atoms, linear and branched $C_1$-$C_4$ alkyl groups optionally substituted by a substituent selected from nitrile groups, a carboxylic acid group, derivatives of a carboxylic acid group, a hydroxyl group, groups:

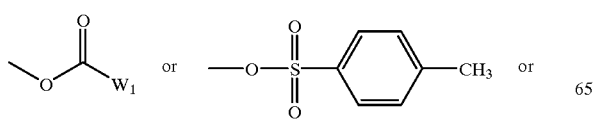

-continued

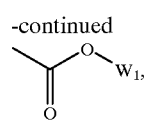

ether groups —OSi(W$_1$)$_3$, amino groups

and amido groups

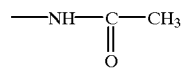

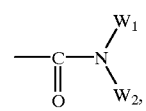

Z is selected from a hydrogen atom, a benzyl group, a phenyl group optionally substituted by a substituent selected from a hydroxyl group, groups —O—CO—W$_1$, amino groups —N(W$_1$)(W$_2$), groups —NH—CO—W$_1$ and a nitrile group; linear and branched $C_1$-$C_8$ alkyl groups optionally substituted by a substituent selected from a nitrile group, a carboxylic acid group, derivatives of a carboxylic acid group, a hydroxyl group, groups:

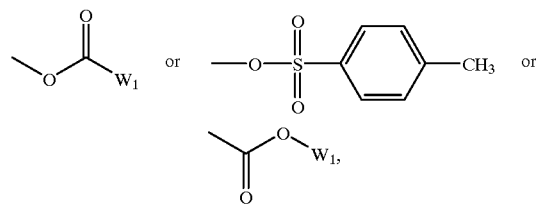

ether groups —OSi(W$_1$)$_3$, amino groups

and amido groups

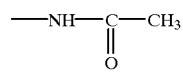

or

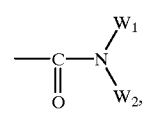

W₁ and W₂, which are identical or different, are selected from a hydrogen atom and linear and branched C₁–C₄ alkyl groups, W₃ and W₄, which are identical or different, are selected from a hydrogen atom and linear and branched C₁–C₄ alkyl groups optionally substituted by at least one substituent selected from a hydroxyl group, groups —CO—O—W₁, groups —O—CO—W₁, and amino groups —N(W₁)(W₂).

2. The composition according to claim 1, wherein said keratin fibers are human keratin fibers.

3. The composition according to claim 2, wherein said human keratin fibers are human hair.

4. The composition according to claim 1, wherein said derivatives of a carboxylic acid group are chosen from esters, amides, mineral salts and organic amine salts.

5. The composition according to claim 1, wherein said at least one dye chosen from formulae (I) and (II) is chosen from:

6-(1-pentyl-1H-pyrrol-2-yl)quinoline-5,8-dione,
6-(1-benzyl-1H-pyrrol-2-yl)quinoline-5,8-dione,
methyl 4-(5,8-dioxo-5,8-dihydroquinolin-6-yl)-2,5-dimethyl-1H-pyrrole-3-carboxylate,
N-[2-[2-(5,8-dioxo-5,8-dihydroquinolin-6-yl)pyrrol-1-yl]ethyl]acetamide,
6-(1-phenyl-1H-pyrrol-2-yl)quinoline-5,8-dione,
3-[2-(5,8-dioxo-5,8-dihydroquinolin-6-yl)pyrrol-1-yl]propionitrile,
6-chloro-7-(1-methyl-1H-pyrrol-2-yl)quinoline-5,8-dione,
6-(1,2-dimethyl-1H-indol-3-yl)quinoline-5,8-dione,
6-(1-benzyl-1H-indol-3-yl)quinoline-5,8-dione,
6-(2-phenyl-1H-indol-3-yl)quinoline-5,8-dione,
6-(1-methyl-1H-indol-3-yl)quinoline-5,8-dione,
6-(2-methyl-1H-indol-3-yl)quinoline-5,8-dione,
6-[p-(N,N-(2-diacetyloxyethyl)amino)phenyl]-quinotine-5,8-dione,
6-(1-methyl-1H-pyrrol-2-yl)quinoxaline-5,8-dione,
6-(1-methyl-1H-pyrrol-2-yl)quinoline-5,8-dione,
7-(1-methyl-1H-pyrrol-2-yl)quinoline-5,8-dione,
6-[p-(N,N-diethylamino)phenyl]quinoline-5,8-dione,
6-[p-(N,N-dimethylamino)phenyl]quinoline-5,8-dione,
7-[p-(N,N-dimethylamino)phenyl]quinoline-5,8-dione,
6-[4-(N,N-diethylamino)-2-isopropenylphenyl]-quinoline-5,8-dione,
6-[4-(N,N-diethylamino)-2-(N-acetylamino)phenyl]quinoline-5,8-dione,
6-[4-(N,N-dimethylamino)-2-isopropenylphenyl]-quinoline-5,8-dione,
6-[4-(N,N-di-n-butylamino)-2-hydroxyphenyl]-quinoline-5,8-dione,
6-[p-(N-n-butylamino)phenyl]quinoline-5,8-dione,
6-[p-(N-methylamino)phenyl]quinoline-5,8-dione,
6-(1-methyl-1H-pyrrol-2-yl)quinoline-5,8-diol, and
7-(1-methyl-1H-pyrrol-2-yl)quinoline-5,8-diol.

6. The composition according to claim 1, wherein said at least one dye of formulae (I) and (II) is chosen from:

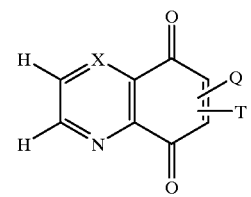

(I)

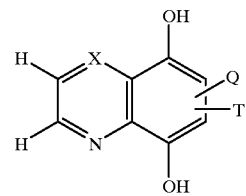

(II)

wherein,

X is a —CH group;

T is a hydrogen atom;

Q is chosen from the formulae below:

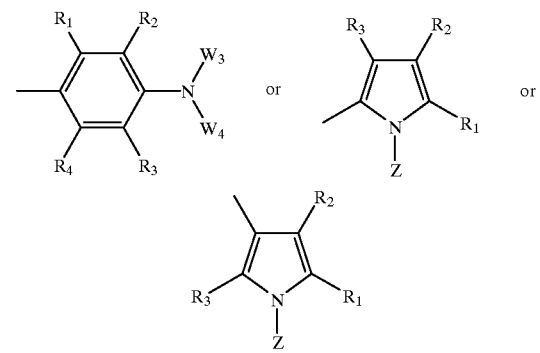

wherein,

R₁ is chosen from a hydrogen atom and —OH;

R₂, R₃, R₄, and R₅ are hydrogen atoms;

Z is chosen from a hydrogen atom and —CH₃, phenyl, benzyl and 2-cyanoethyl groups; and W₃ and W₄ are chosen from a hydrogen atom and methyl, ethyl and n-butyl groups.

7. A composition for the dyeing of keratin fibers comprising a cosmetically acceptable medium and an amount effective for dyeing keratin fibers of at least one dye chosen from general formulae (III) and (IV) below:

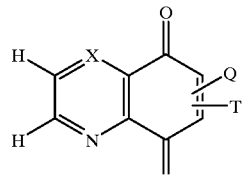

(III)

-continued

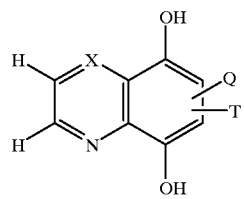
(IV)

wherein,

X represents the group CH or a nitrogen atom;

T represents a hydrogen atom, a halogen atom or a hydroxyl group;

Q is chosen from the formulae below:

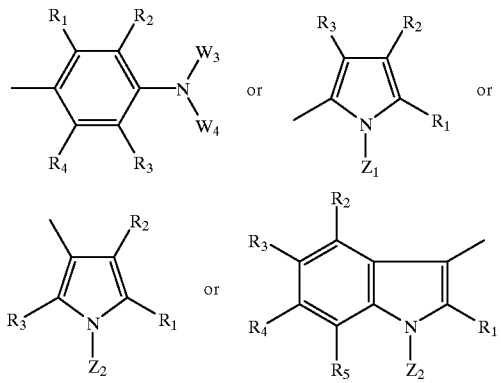

wherein, $R_1$, $R_2$, $R_3$, $R_4$ and $R_5$, which are identical or different, are selected from a hydrogen atom, $C_1$–$C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, halogen atoms, linear and branched $C_1$–$C_4$ alkyl groups optionally substituted by a substituent selected from a nitrile group, a carboxylic acid group, derivatives of a carboxylic acid group, a hydroxyl group, groups:

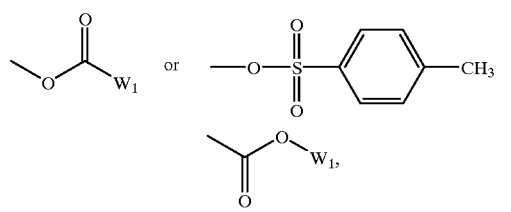

ether groups —OSi($W_1$)$_3$, amino groups

and amido groups

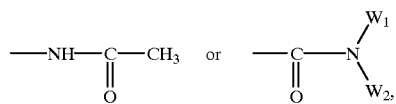

$Z_2$ represents a hydrogen atom, a benzyl group, a phenyl group optionally substituted by a substituent selected from a hydroxyl group, groups —CO—O—$W_1$, groups —O—CO—$W_1$, amino groups —N($W_1$)($W_2$), amino groups —CO—N($W_1$)($W_2$), amino groups —NH—CO—$W_1$ and a nitrile group; linear and branched $C_1$–$C_8$ alkyl groups optionally substituted by a substituent selected from a nitrile group, a carboxylic acid group, derivatives of a carboxylic acid group, a hydroxyl group, groups:

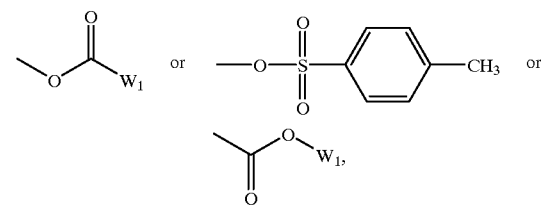

ether groups —OSi($W_1$)$_3$, amino groups

and amido groups

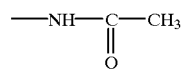

or

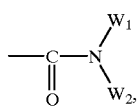

$Z_1$ has the same meanings as $Z_2$ with the proviso that $Z_1$ is not methyl in the cases where T=H and X=CH, $W_1$ and $W_2$, which are identical or different, are selected from a hydrogen atom and linear and branched $C_1$–$C_4$ alkyl groups, $W_4$ is selected from a hydrogen atom and linear and branched $C_1$–$C_4$ alkyl groups, optionally substituted by at least one substituent selected from a hydroxyl group, groups —CO—O—$W_1$, groups —O—CO—$W_1$, and amino groups —N($W_1$)($W_2$), and $W_3$ has the same meanings as $W_4$ with the proviso that, when one of the substituents $W_3$ and $W_4$ represents a hydrogen atom, the other substituent does not represent a methyl or n-butyl group; and, when the substituents $W_3$ and $W_4$ are identical, they do not represent either a methyl group or an ethyl group.

8. A composition for the dyeing of keratin fibers comprising a cosmetically acceptable medium and an amount effective for dyeing keratin fibers of at least one dye chosen from:

6-(1-pentyl-1H-pyrrol-2-yl)quinoline-5,8-dione, 6-(1-benzyl-1H-pyrrol-2-yl)quinoline-5,8-dione, methyl 4-(5,8-dioxo-5,8-dihydroquinolin-6-yl)-2,5-dimethyl-1H-pyrrole-3-carboxylate, N-[2-[2-(5,8-dioxo-5,8-dihydroquinolin-6-yl)pyrrol-1-yl]ethyl]acetamide, 6-(1-phenyl-1H-pyrrol-2-yl)quinoline-5,8-dione, 3-[2-(5,8-dioxo-5,8-dihydroquinolin-6-yl)pyrrol-1-yl]propionitrile, 6-chloro-7-(1-methyl-1H-pyrrol-2-yl)quinoline-5,8-dione, 6-(1,2-dimethyl-1H-indol-3-yl)quinoline-5,8-dione, 6-(1-benzyl-1H-indol-3-yl)quinoline-5,8-dione, 6-[p-(N,N-(2-diacetyloxyethyl)amino)phenyl]-quinoline-5,8-dione, 6-(2-phenyl-1H-indol-3-yl)quinoline-5,8-dione, 6-(1-methyl-1H-indol-3-yl)quinoline-5,8-dione, 6-(2-methyl-1H-indol-3-yl)quinoline-5,8-dione, and 6-(1-methyl-1H-pyrrol-2-yl)quinoxaline-5,8-dione.

9. A composition for the dyeing of keratin fibers comprising a cosmetically acceptable medium and an amount effective for dyeing keratin fibers of at least one dye chosen from general formulae (III) and (IV) below:

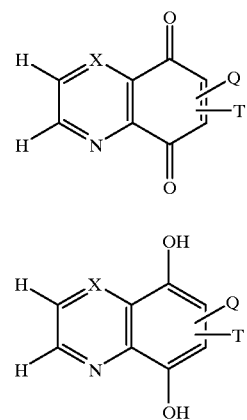

(III)

(IV)

wherein,

X is chosen from —CH and —N;

T is a hydrogen atom;

Q is chosen from formulae below:

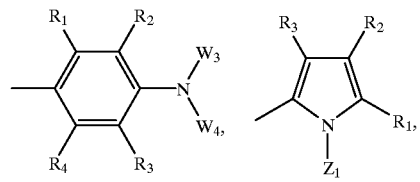

-continued

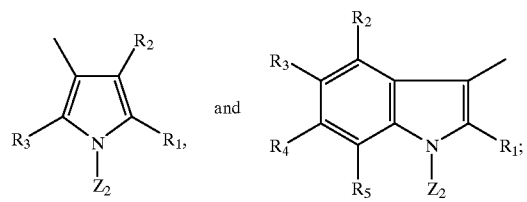

and wherein further, $R_1$ is chosen from —H and —$CH_3$ groups;

$R_2$ is chosen from —H and —COO—$W_1$ groups;

$R_3$ is chosen from —H and methyl groups;

$R_4$ and $R_5$ are both H;

$W_1$ is a —$CH_3$ group;

$Z_1$ is chosen from —$C_5H_{11}$, —$(CH_2)_2$—NH—$COCH_3$, —$(CH_2)_2$—CN, and phenyl groups;

$Z_2$ is chosen from —H, —$CH_3$, and benzyl groups; and $W_3$ and $W_4$ are chosen from —$(CH_2)_2OCOW_1$ groups.

10. A method for the direct dyeing of keratin fibers, comprising applying to keratin fibers a composition in an amount effective to achieve said direct dyeing, wherein said composition comprises at least one dye of general formulae (I) and (II) below:

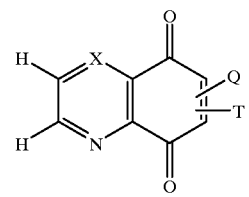

(I)

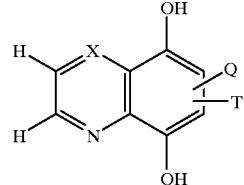

(II)

wherein:

T is chosen from a hydrogen atom, halogen atoms and a hydroxyl group;

X is chosen from a —CH group and a nitrogen atom;

Q is chosen from the groups below:

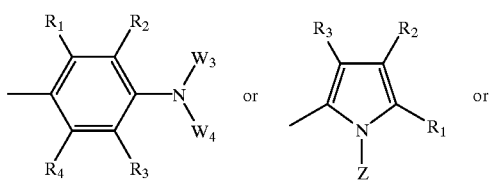

or or

-continued

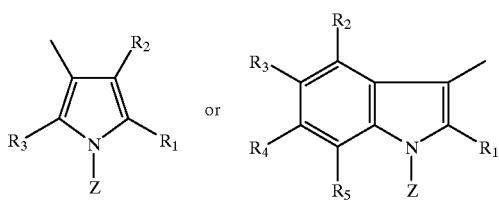

wherein in said groups:

$R_1$, $R_2$, $R_3$, $R_4$ and $R_5$, which are identical or different, are selected from a hydrogen atom, $C_1$–$C_4$ alkoxy groups, amino groups —$N(W_1)(W_2)$, groups —NH—CO—$W_1$, groups —O—CO—$W_1$, a hydroxyl group, a carboxylic acid group, derivatives of a carboxylic acid group, halogen atoms, linear and branched $C_1$–$C_4$ alkyl groups optionally substituted by a substituent selected from nitrile groups, a carboxylic acid group, derivatives of a carboxylic acid group, a hydroxyl group, groups:

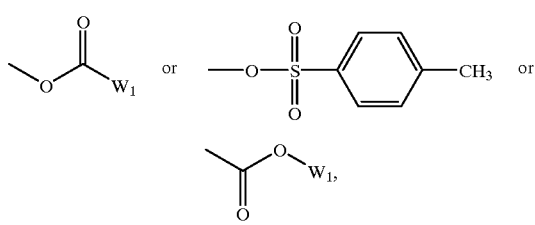

ether groups —$OSi(W_1)_3$, amino groups

and amido groups

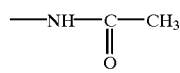

or

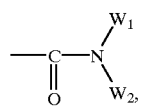

Z is selected from a hydrogen atom, a benzyl group, a phenyl group optionally substituted by a substituent selected from a hydroxyl group, groups —O—CO—$W_1$, amino groups —$N(W_1)(W_2)$, groups —NH—CO—$W_1$ and a nitrile group; linear and branched $C_1$–$C_8$ alkyl groups optionally substituted by a substituent selected from a nitrile group, a carboxylic acid group, derivatives of a carboxylic acid group, a hydroxyl group, groups:

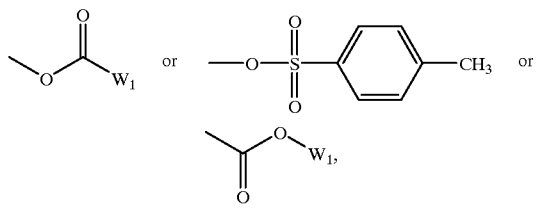

ether groups —$OSi(W_1)_3$, amino groups

and amido groups

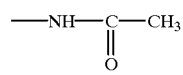

or

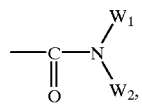

$W_1$ and $W_2$, which are identical or different, are selected from a hydrogen atom and linear and branched $C_1$–$C_4$ alkyl groups, $W_3$ and $W_4$, which are identical or different, are selected from a hydrogen atom and linear and branched $C_1$–$C_4$ alkyl groups optionally substituted by at least one substituent selected from a hydroxyl group, groups —CO—O—$W_1$, groups —O—CO—$W_1$, and amino groups —$N(W_1)(W_2)$.

11. A composition for the oxidation dyeing of hair comprising a cosmetically acceptable medium and an amount effective for dyeing hair of at least one direct dye chosen from general formulae (I) and (II) below:

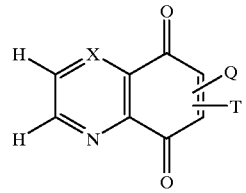 (I)

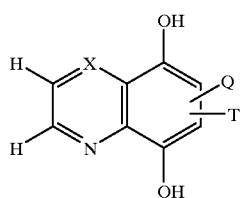 (II)

wherein:

T is chosen from a hydrogen atom, halogen atoms and a hydroxyl group;

X is chosen from a —CH group and a nitrogen atom;
Q is chosen from the groups below:

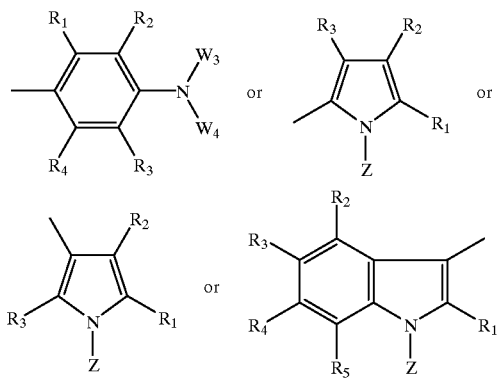

wherein in said groups:
$R_1$, $R_2$, $R_3$, $R_4$ and $R_5$, which are identical or different, are selected from a hydrogen atom, $C_1$–$C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, halogen atoms, linear and branched $C_1$–$C_4$ alkyl groups optionally substituted by a substituent selected from nitrile groups, a carboxylic acid group, derivatives of a carboxylic acid group, a hydroxyl group, groups:

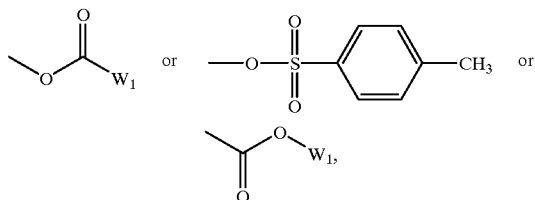

ether groups —OSi($W_1$)$_3$, amino groups

and amido groups

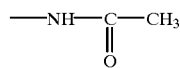

or

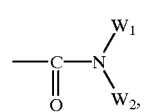

Z is selected from a hydrogen atom, a benzyl group, a phenyl group optionally substituted by a substituent selected from a hydroxyl group, groups —O—CO—$W_1$, amino groups —N($W_1$)($W_2$), groups —NH—CO—$W_1$ and a nitrile group; linear and branched $C_1$–$C_8$ alkyl groups optionally substituted by a substituent selected from a nitrile group, a carboxylic acid group, derivatives of a carboxylic acid group, a hydroxyl group, groups:

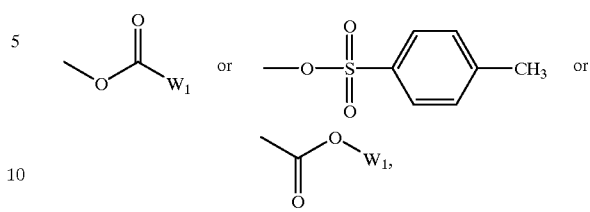

ether groups —OSi($W_1$)$_3$, amino groups

and amido groups

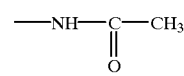

or

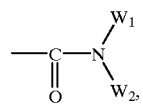

$W_1$ and $W_2$, which are identical or different, are selected from a hydrogen atom and linear and branched $C_1$–$C_4$ alkyl groups, $W_3$ and $W_4$, which are identical or different, are selected from a hydrogen atom and linear and branched $C_1$–$C_4$ alkyl groups optionally substituted by at least one substituent selected from a hydroxyl group, groups —CO—O—$W_1$, groups —O—CO—$W_1$, and amino groups —N($W_1$)($W_2$).

12. A method for the progressive dyeing of keratin fibers, comprising applying a composition to said keratin fibers, exposing the fibers to atmospheric oxygen, rinsing and drying said fibers, and repeating the steps until desired coloration is achieved, wherein said composition comprises at least one dye of general formula (II) below:

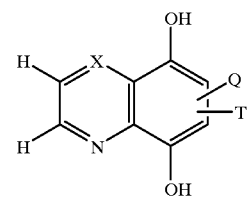

(II)

wherein:
T is chosen from a hydrogen atom, halogen atoms and a hydroxyl group;
X is chosen from a —CH group and a nitrogen atom;

Q is chosen from the groups below:

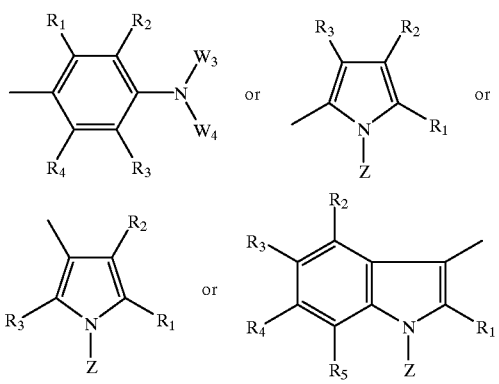

wherein in said groups:

$R_1$, $R_2$, $R_3$, $R_4$ and $R_5$, which are identical or different, are selected from a hydrogen atom, $C_1$–$C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, halogen atoms, linear and branched $C_1$–$C_4$ alkyl groups optionally substituted by a substituent selected from nitrile groups, a carboxylic acid group, derivatives of a carboxylic acid group, a hydroxyl group, groups:

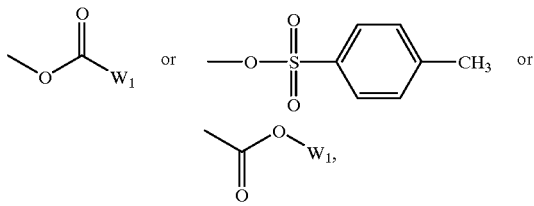

ether groups —OSi($W_1$)$_3$, amino groups

and amino groups

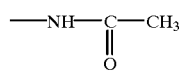

or

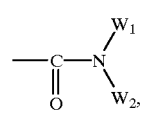

Z is selected from a hydrogen atom, a benzyl group, a phenyl group optionally substituted by a substituent selected from a hydroxyl group, groups —O—CO—$W_1$, amino groups —N($W_1$)($W_2$), groups —NH—CO—$W_1$ and a nitrile group; linear and branched $C_1$–$C_8$ alkyl groups optionally substituted by a substituent selected from a nitrile group, a carboxylic acid group, derivatives of a carboxylic acid group, a hydroxyl group, groups:

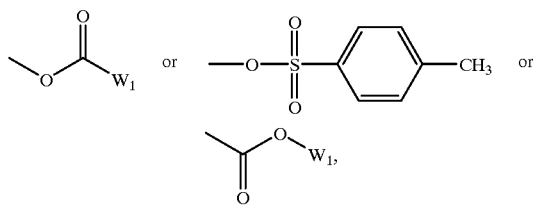

ether groups —OSi($W_1$)$_3$, amino groups

and amido groups

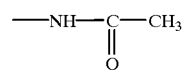

or

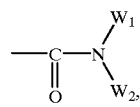

$W_1$ and $W_2$, which are identical or different, are selected from a hydrogen atom and linear and branched $C_1$–$C_4$ alkyl groups, $W_3$ and $W_4$, which are identical or different, are selected from a hydrogen atom and linear and branched $C_1$–$C_4$ alkyl groups optionally substituted by at least one substituent selected from a hydroxyl group, groups —CO—O—$W_1$, groups —O—CO—$W_1$, and amino groups —N($W_1$)($W_2$).

13. A compound selected from formulae (I) and (II) below:

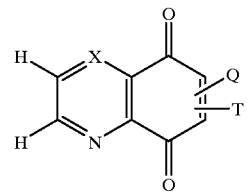

(I)

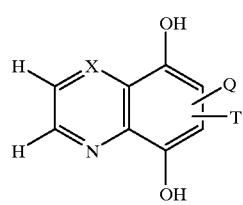

(II)

wherein:

T is chosen from a hydrogen atom, halogen atoms and a hydroxyl group;

X is chosen from a —CH group and a nitrogen atom;
Q is chosen from the groups below:

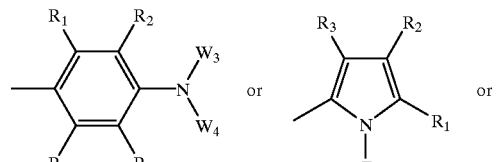

or

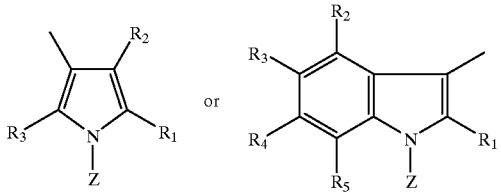

wherein in said groups:
$R_1$, $R_2$, $R_3$, $R_4$ and $R_5$, which are identical or different, are selected from a hydrogen atom, $C_1$-$C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, halogen atoms, linear and branched $C_1$-$C_4$ alkyl groups optionally substituted by a substituent selected from nitrile groups, a carboxylic acid group, derivatives of a carboxylic acid group, a hydroxyl group, groups:

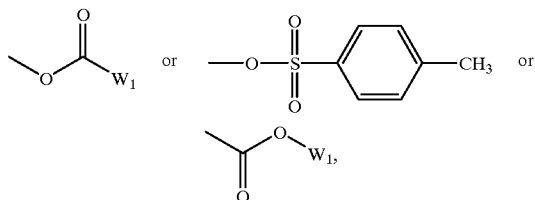

ether groups —OSi($W_1$)$_3$, amino groups

and amido groups

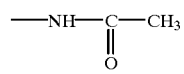

or

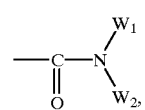

Z is selected from a hydrogen atom, a benzyl group, a phenyl group optionally substituted by a substituent selected from a hydroxyl group, groups —O—CO—$W_1$, amino groups —N($W_1$)($W_2$), groups —NH—CO—$W_1$ and a nitrile group; linear and branched $C_1$-$C_8$ alkyl groups optionally substituted by a substituent selected from a nitrile group, a carboxylic acid group, derivatives of a carboxylic acid group, a hydroxyl group, groups:

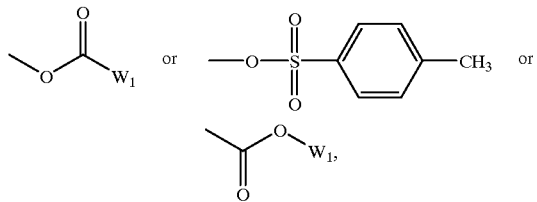

ether groups —OSi($W_1$)$_3$, amino groups

and amido groups

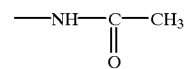

or

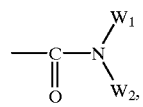

$W_1$ and $W_2$, which are identical or different, are selected from a hydrogen atom and linear and branched $C_1$-$C_4$ alkyl groups,
$W_3$ and $W_4$, which are identical or different, are selected from a hydrogen atom and linear and branched $C_1$-$C_4$ alkyl groups optionally substituted by at least one substituent selected from a hydroxyl group, groups —CO—O—$W_1$, groups —O—CO—$W_1$, and amino groups —N($W_1$)($W_2$) with the proviso that:
when Q represents

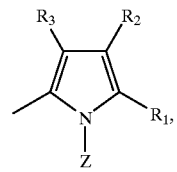

X=CH and T=H, then Z is other than the methyl group;
when Q represents

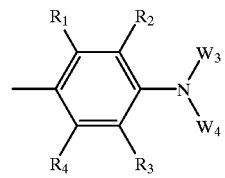

and one of the substituents $W_3$ and $W_4$ represents a hydrogen atom, the other substituent does not represent a methyl or n-butyl group; and when Q represents

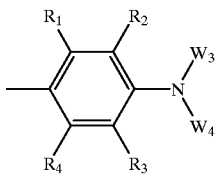

and the substituents $W_3$ and $W_4$ are identical, they do not represent either a methyl group or an ethyl group.

14. A compound selected from the following compounds:

6-(1-pentyl-1H-pyrrol-2-yl)quinoline-5,8-dione,
6-(1-benzyl-1H-pyrrol-2-yl)quinoline-5,8-dione,
methyl 4-(5,8-dioxo-5,8-dihydroquinolin-6-yl)-2,5-dimethyl-1H-pyrrole-3-carboxylate,
N-[2-[2-(5,8-dioxo-5,8-dihydroquinolin-6-yl)pyrrol-1-yl]ethyl]acetamide,
6-(1-phenyl-1H-pyrrol-2-yl)quinoline-5,8-dione,
3-[2-(5,8-dioxo-5,8-dihydroquinolin-6-yl)pyrrol-1-yl] propionitrile,
6-chloro-7-(1-methyl-1H-pyrrol-2-yl)quinoline-5,8-dione,
6-(1,2-dimethyl-1H-indol-3-yl)quinoline-5,8-dione,
6-(1-benzyl-1H-indol-3-yl)quinoline-5,8-dione,
6-[p-(N,N-(2-diacetyloxyethyl)amino)phenyl]-quinoline-5,8-dione,
6-(2-phenyl-1H-indol-3-yl)quinoline-5,8-dione,
6-(1-methyl-1H-indol-3-yl)quinoline-5,8-dione,
6-(2-methyl-1H-indol-3-yl)quinoline-5,8-dione,
6-(1-methyl-1H-pyrrol-2-yl)quinoxaline-5,8-dione.

15. A method of dyeing human keratinous fibres comprising applying a dyeing composition of claim 1 to the keratinous fibres and, after a time sufficient to develop a desired colouration, rinsing the fibres, washing the fibres, rinsing again and drying.

16. A method of dyeing human keratinous fibres comprising applying a dyeing composition of claim 1 to the keratinous fibres for a time sufficient to develop a desired colouration without final rinsing.

17. A compound selected from formulae (I) and (II) below:

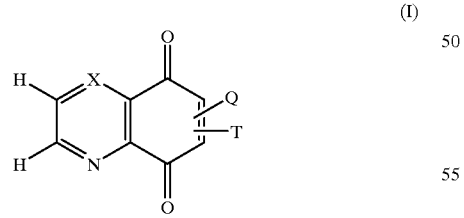

(I)

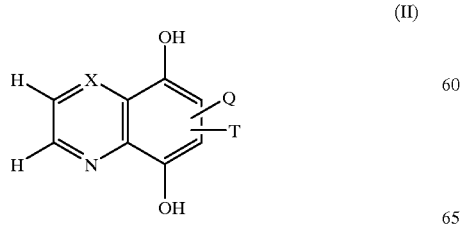

(II)

wherein:
T is chosen from a hydrogen atom, halogen atoms and a hydroxyl group;
X is chosen from a —CH group and a nitrogen atom;
Q is chosen from the groups below:

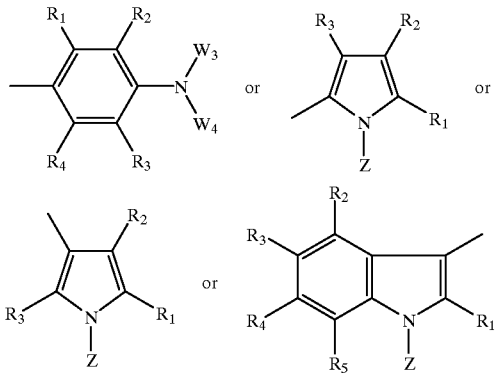

wherein in said groups:
$R_1$, $R_2$, $R_3$, $R_4$ and $R_5$, which are identical or different, are selected from a hydrogen atom, $C_1$–$C_4$ alkoxy groups, amino groups —N($W_1$)($W_2$), groups —NH—CO—$W_1$, groups —O—CO—$W_1$, a hydroxyl group, a carboxylic acid group, derivatives of a carboxylic acid group, halogen atoms, linear and branched $C_1$–$C_4$ alkyl groups optionally substituted by a substituent selected from nitrile groups, a carboxylic acid group, derivatives of a carboxylic acid group, a hydroxyl group, groups:

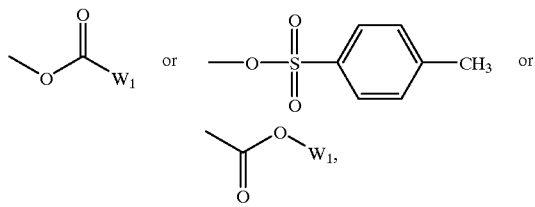

ether groups —OSi($W_1$)$_3$, amino groups

and amido groups

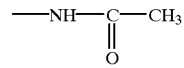

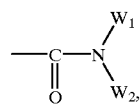

Z is selected from a hydrogen atom, a benzyl group, a phenyl group optionally substituted by a substituent selected from a hydroxyl group, groups —O—CO—$W_1$, amino groups —N($W_1$)($W_2$), groups —NH—CO—$W_1$ and a nitrile group; linear and branched $C_1$–$C_8$ alkyl groups optionally substituted by a substituent selected from a nitrile group, a carboxylic acid group, derivatives of a carboxylic acid group, a hydroxyl group, groups:

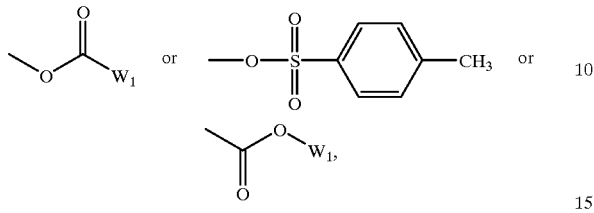

ether groups —OSi($W_1$)$_3$, amino groups

and amido groups

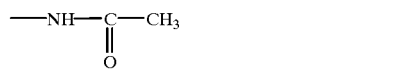

or

$W_1$ and $W_2$, which are identical or different, are selected from a hydrogen atom and linear and branched $C_1$–$C_4$ alkyl groups, $W_3$ and $W_4$, which are identical or different, are selected from a hydrogen atom and linear and branched $C_1$–$C_4$ alkyl groups optionally substituted by at least one substituent selected from a hydroxyl group, groups —CO—O—$W_1$, groups —O—CO—$W_1$, and amino groups —N($W_1$)($W_2$)

with the proviso that:

when Q represents

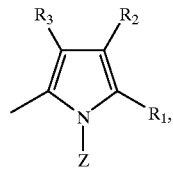

X=CH and T=H, then Z is other than the methyl group;

Q does not represent

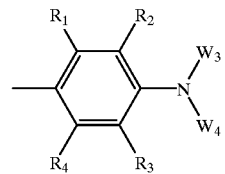

in formula (I); and when Q represents

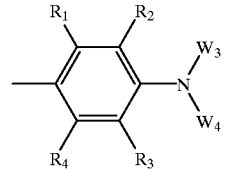

in formula (II) and the substituents $W_3$ and $W_4$ are identical, they do not represent a methyl group.

* * * * *

UNITED STATES PATENT AND TRADEMARK OFFICE
CERTIFICATE OF CORRECTION

PATENT NO.    : 6,391,064 B1
DATED         : May 21, 2002
INVENTOR(S)   : Richard Baudry et al.

It is certified that error appears in the above-identified patent and that said Letters Patent is hereby corrected as shown below:

<u>Title page,</u>
Item [54], in the title "QUINOLINE-5, 8-DIONES" should read -- QUINOLINE-5,8-DIONES --;

<u>Column 18,</u>
Line 20, after the third structure from the top of the column, insert -- or --;

<u>Column 19,</u>
Line 42, "quinotine" should read -- quinoline --;

<u>Column 27,</u>
Line 54, after the second structure from the bottom of the column, insert -- or --;

<u>Column 29,</u>
Line 48, "amino" should read -- amido --;
Line 54, after the second structure from the bottom of the column, insert -- or --;

<u>Column 31,</u>
Line 54, after the second structure from the bottom of the column, insert -- or --; and <u>Column 34,</u>
Line 58, after the second structure from the bottom of the column, insert -- or --.

Signed and Sealed this

Seventeenth Day of September, 2002

*Attest:*

JAMES E. ROGAN
*Attesting Officer*  *Director of the United States Patent and Trademark Office*